US009283383B2

(12) United States Patent
Osypka

(10) Patent No.: US 9,283,383 B2
(45) Date of Patent: Mar. 15, 2016

(54) IMPLANTABLE EPICARDIAL ELECTRODE ASSEMBLY

(76) Inventor: Peter Osypka, Grenzach-Wyhlen (DE)

(*) Notice: Subject to any disclaimer, the term of this patent is extended or adjusted under 35 U.S.C. 154(b) by 0 days.

(21) Appl. No.: 14/241,091

(22) PCT Filed: Aug. 16, 2012

(86) PCT No.: PCT/DE2012/000825
§ 371 (c)(1),
(2), (4) Date: Feb. 26, 2014

(87) PCT Pub. No.: WO2013/029587
PCT Pub. Date: Mar. 7, 2013

(65) Prior Publication Data
US 2014/0194965 A1 Jul. 10, 2014

(30) Foreign Application Priority Data

Aug. 26, 2011 (DE) .......................... 10 2011 111 649

(51) Int. Cl.
A61N 1/05 (2006.01)
A61N 1/39 (2006.01)
A61N 1/362 (2006.01)

(52) U.S. Cl.
CPC .............. A61N 1/059 (2013.01); A61N 1/0597 (2013.01); A61N 1/3625 (2013.01); A61N 1/3918 (2013.01); A61N 1/3956 (2013.01)

(58) Field of Classification Search
None
See application file for complete search history.

(56) References Cited

U.S. PATENT DOCUMENTS

| 4,774,952 | A | * | 10/1988 | Smits ..................... A61N 1/056 607/2 |
| 5,063,932 | A | * | 11/1991 | Dahl ..................... A61N 1/0587 600/374 |
| 7,640,065 | B1 | | 12/2009 | Kroll |
| 2007/0043416 | A1 | | 2/2007 | Callas et al. |
| 2007/0073218 | A1 | * | 3/2007 | Lau et al. .................. 604/93.01 |
| 2007/0106336 | A1 | | 5/2007 | Schaer et al. |
| 2007/0106359 | A1 | | 5/2007 | Schaer et al. |
| 2011/0196451 | A1 | * | 8/2011 | Hill ................................ 607/60 |

OTHER PUBLICATIONS

PCT International Search Report dated Dec. 19, 2012 issued on corresponding International Patent Application No. PCT/DE2012/000825.

* cited by examiner

Primary Examiner — Brian T Gedeon
Assistant Examiner — Ankit Tejani
(74) Attorney, Agent, or Firm — Locke Lord LLP; Scott D. Wofsy; Daniel J. Fiorello

(57) ABSTRACT

An implantable epicardial electrode assembly comprises electrode poles fixed on the heart having a large surface area and being multipolar and can at the same time be used as sensing and stimulating electrodes, wherein the electrode assembly has the shape of a tennis racket or is circular, elliptical, hexagonal, rectangular, oakleaf-shaped, star-shaped or cloverleaf-shaped and comprises at least two electrode poles which are arranged over a large surface area, and a further electrode arrangement which comprises at least one electrode pole and which is arranged between the large surface area electrode poles and further comprises a fixing element, wherein the defibrillation can take place between the mutually insulated poles of the electrodes, and wherein the stimulation of the heart can take place between one of the electrode poles and a pole of the electrode arrangement.

8 Claims, 3 Drawing Sheets

IMPLANTABLE EPICARDIAL ELECTRODE ASSEMBLY

CROSS-REFERENCE TO RELATED APPLICATIONS

This application claims priority to and the benefit of PCT/DE2012/000825, filed Aug. 16, 2012, which claims priority to German Patent Application No. DE102011111649, filed Aug. 26, 2011, the entire contents of each being incorporated herein.

FIELD

The invention relates to an implantable epicardial electrode assembly and the fixation of said assembly.

BACKGROUND

Atrial fibrillation occurs with increasing age and after cardiac surgery relatively frequently and is one of the main reasons for postoperative morbidity.

In recent years the occurrence of atrial fibrillation appears to have increased in general, and particularly after cardiac surgery, due to the fact that patients are getting older and older. According to information based on literature references 30%-40% of the patients with no prior arrhythmia suffer from post-operative atrial fibrillation after heart bypass surgery.

Atrial fibrillation leads to a rapid transfer of the electrical excitation to the ventricles, so that acute hemodynamic instability may occur. The current external electrical cardioversion technique is a non-drug and very effective method of restoring sinus rhythm, however, requires a short anesthesia. This short anesthesia may aggravate the existing neural problems (vigilance) in patients after having successfully endured a heart surgery especially a bypass surgery. The neural problems can lead to a prolonged recovery period or even require a re-intubation and mechanical ventilation.

Another problem is the necessity of an anticoagulation therapy in postoperative patients having atrial fibrillation. If the arrhythmia continues for longer than 24 hours, anticoagulation therapy is required in order to reduce thrombus formation with the risk of stroke. All these factors lead to a complicated postoperative healing in patients after bypass surgery, requiring prolonged hospitalization of about 5 days and thus increasing the costs. Atrial fibrillation can occur repeatedly during the patients stay in intensive care. Literature references describe the so-called "multi-site pacing" for the prophylaxis of atrial fibrillation whereby several areas of the left atrium are simultaneously stimulated.

"Multi-site pacing" is performed using unipolar heart wires which are operated against an external anode.

Due to the anatomical position of the left atrium, the fixation of multiple electrodes is particularly difficult, which may lead to frequent stimulation failure during the therapy. The cause of re-occurrence of atrial fibrillation has not yet been extensively researched due to lack of suitable electrodes so far. How is the problem solved so far?

To stop atrial fibrillation defibrillation is a routine procedure whereby an electric shock is used to reset the heart's rhythm back to the normal sinus rhythm. The external electric energy pulse enters the body through large area metal paddles or patches applied to the chest wall. Before atrial defibrillation is applied an ultrasound examination of the left atrial appendage is necessary. Furthermore the defibrillation procedure is performed under anesthetic.

There are literature references describing methods to stop atrial fibrillation after cardiac surgery, whereby a bare strand is positioned at each atrium and whereby the cardioversion takes place between the atria. The necessary shock energy is between 5-9 joules and therefore causes significant pain.

There is therefore a need to provide an electrode assembly which is well anchored and which allows a stable temporary stimulation or multi-site pacing. Furthermore the electrode assembly should allow a painless cardioversion procedure for stopping atrial fibrillation and should allow prophylaxis to prevent re-occurrence of atrial fibrillation.

Due to the fact that the cardioversion is performed using electrode assemblies wherein the assembly is used epicardial, locally and temporarily at the two atria, the necessary electrical energy output for cardioversion is reduced significantly.

Using the electrode assembly as disclosed herein, the re-occurrence of atrial fibrillation may be prevented or may be treated immediately without the necessity of anesthesia. After the cardioversion the electrode assemblies can be removed as easily as commonly used heart wires are removed.

Temporary myocardial leads (also known as heart wires) allow an external stimulation of the heart after a heart surgery. Such electrodes have been known for many years and are used routinely after each open-heart surgery for the stimulation of the atria and ventricles. The fixation of the leads at the heart surface must be such that on the one hand, the leads are fixed stably during the patient's stay in the intensive care unit (ICU), on the other hand the leads must be easily removable through a small opening in the abdominal wall of the patient.

Common fixing methods for fixing the leads temporarily at the cardiac muscle are shown in FIG. 1. Fixing methods whereby suture material is left in the cardiac muscle after removal of the myocardial lead are not always acceptable, especially not when fixing the myocardial lead on small hearts of children. Even the plastic helix used for fixation and the zig-zag fixation element are often too large for such applications. Fixation elements in shape of a plastic anchor are very often used. The disadvantage of the plastic anchor is the indefinite area of the electrode. The anchor is in shape of three strips which are cut out from the insulation of the strand. The rest of the remaining strand is the different pole. Since this area is very small, every little physical movement causes a threshold change.

There is a need to provide a fixation of heart wires as described above which allows good anchorage and a stable temporary pacing of the heart.

SUMMARY

The electrode assembly permits measurement, monitoring, stimulation and defibrillation (cardioversion) of the human heart and is used in conjunction with an external heart pacemaker or defibrillator which is positioned outside the body. The electrode assembly can be easily removed at any time after use by being pulled out. The electrode poles of said assembly fixed on the heart surface have a large surface area, are multipolar and may be used at the same time as sensing and stimulation electrodes.

BRIEF DESCRIPTION OF THE DRAWINGS

Further details, features and advantages of the invention are found in the following part of the description, wherein the invention will be explained in more detail. The figures show in a schematic representation the following.

The electrode assembly has a pocket-shaped bulge (34) to achieve a better placement at the surface of the heart. The electrode assembly is moved by a suitable pusher which is in the bulge and which is made of plastic or of metal.

Figure 11:
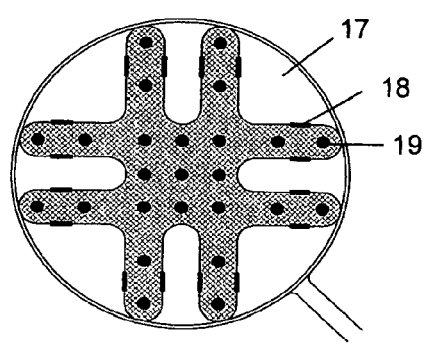

FIG. 11 shows another exemplary electrode assembly (17) for defibrillation (cardioversion) and multipolar stimulation at different parts of the heart. The assembly having the electrodes (18, 19) is cross shaped.

Figure 12:
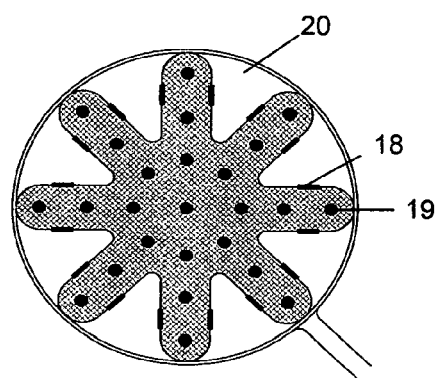

FIG. 12 shows another exemplary electrode assembly (20) for the defibrillation (cardioversion) and multipolar stimulation at different parts of the heart. The assembly having the electrodes (18, 19) is star shaped.

Figure 13:
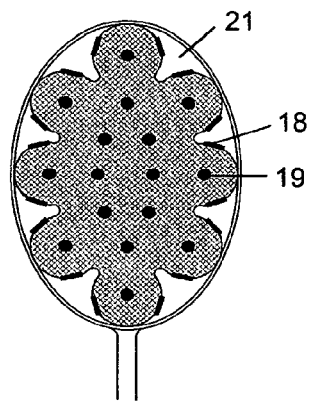

FIG. 13 shows another exemplary electrode assembly (21) for the defibrillation (cardioversion), and multipolar stimulation at different parts of the heart. The assembly is elliptical-like shaped.

Figure 14:
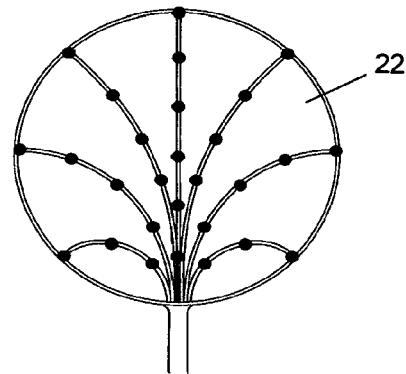

FIG. 14 shows another exemplary electrode assembly for the defibrillation (cardioversion) and multipolar stimulation at different parts of the heart. The electrode poles for stimulation are arranged in shape of a fan.

Figure 15:
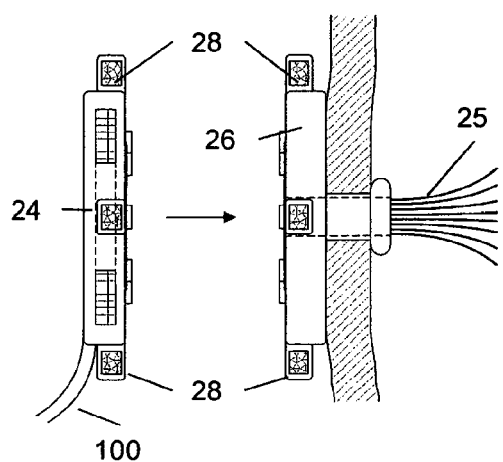

FIG. 15 shows an example for a connection device connecting the inner electrode assembly and the medical equipment to which the electrode assembly must be connected. The connection device is positioned on the outside of the human body.

Figure 16:
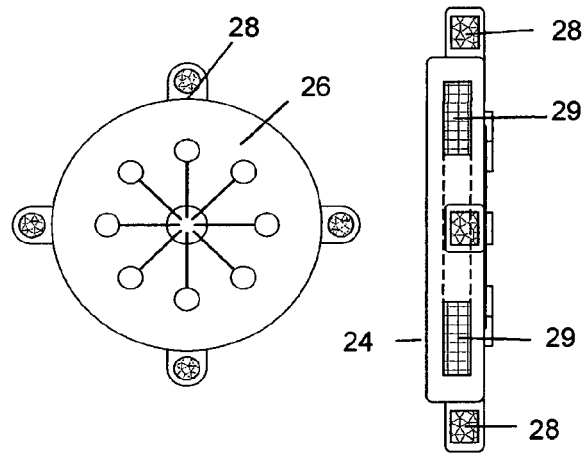

FIG. 16 shows an example for a telemetry device which can transfer the data received from the heart and which also can transfer externally transmitted data, such as electrical pulses to the electrode assembly. This telemetry device may also be implanted subcutaneously.

DETAILED DESCRIPTION

Figure 1:
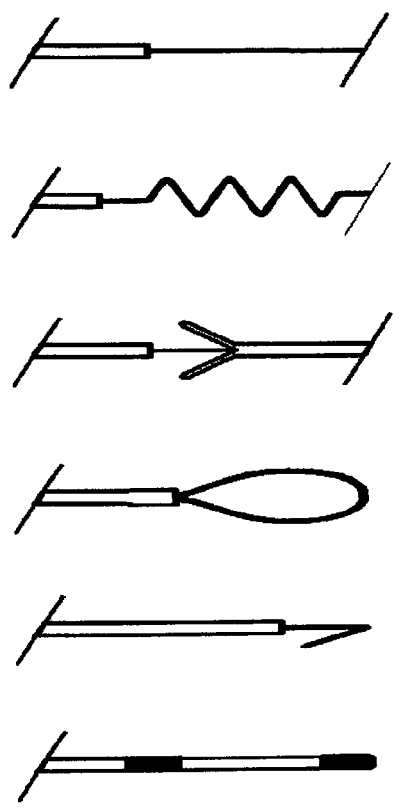
FIG. 1 shows various types of distal end sections of common temporary electrodes made of metal strand and having different types of fixation elements, said electrodes being used for stimulating the heart after a cardiac surgery.

FIG. 1 shows common temporary electrodes made of metal strand and having different types of fixation elements, said electrodes being used for stimulating the heart after a cardiac surgery.

Figure 2:
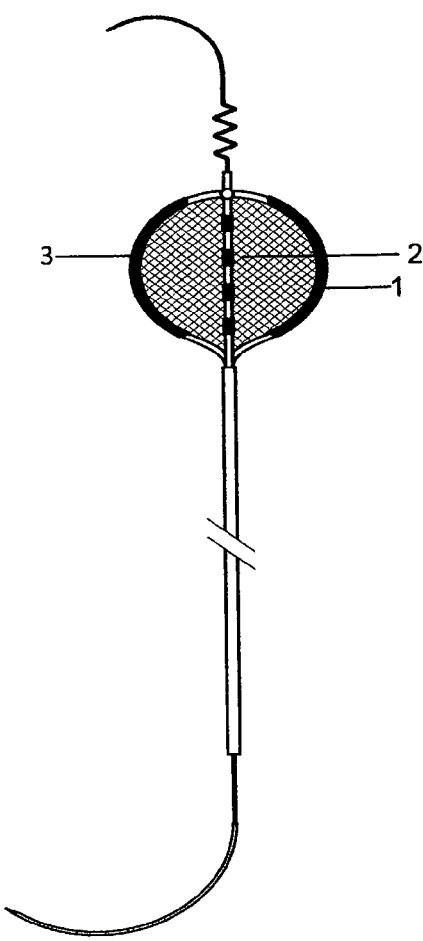
FIG. 2 shows an exemplary electrode assembly for defibrillation (cardioversion) and stimulation of the heart in the shape of a tennis racket.

FIG. 2 shows an exemplary electrode assembly for defibrillation (cardioversion), and stimulation of the heart in the shape of a tennis racket having metal coils (1,3) arranged in a large area. The coils are flexible and are arranged such that the electrode surface is enlarged. The coils can adapt very well to the anatomy of the heart.

The defibrillation can be performed between the two electrode poles of the coil (1,3) which are insulated from each other.

The stimulation of the heart can be performed between one of the electrode poles of (2) and the coil (1), between one of the electrode poles of (2) and coil (3), or between the individual electrode poles (2).

It is important to mention that due to the electrode poles (metal coils) which are arranged in large area the defibrillation can be performed separately on each atrium. Furthermore the shape of the electrode assembly is very important to allow the arrangement of the electrode poles for defibrillation and the electrode poles for stimulation in one device thus solving the problem of difficult fixation of the electrode poles.

The energy required for the defibrillation shock, is less than 5 joules, preferably less than 2 joules, more preferably less than 1 Joule, so that the defibrillation may be effected substantially without pain.

Furthermore the inventive electrode assembly allows a stimulation without the need of fixing any further stimulation electrode.

The diversity of the present invention is shown by describing various embodiments. The electrode poles may be coil shaped or the electrode poles may be a single wire or a multiple parallel coiled wire or a tape. The electrode poles may be blank or may be partially isolated. The electrode poles may have different diameters and may be formed of different materials. Silicone films with a plurality of conductive poles made of metal or conductive plastic may be used. The silicone films should be adapted to the heart contours. Furthermore, the electrode may be constructed of wire mesh, metal strand or parallel conductors.

The design of the novel electrode assembly varies as follows:

Choice of materials: stainless steel, platinum, gold, elgiloy, nitinol, isotan, electrically conductive fibers, carbon fibers, electrically conductive plastic, also mixed with nanoparticles. Isolation: polyurethane, polyethylene, silicone, PTFE, Pebax, polyamide, polyimide, PEEK, all biocompatible plastics incl. coatings.

Construction: Coil, braid, strand, wire, plastic, metal bands, metal pipe, carbon fibers, each adapted to the heart contours. Various wire material in different thickness can be used. The number of wires and plastic threads can vary.

Shape of the assembly: circular, tennis racket-like, elliptical, hexagonal, rectangular, oak leaf-shaped, star-shaped, clover leaf-shaped.

Shape of the electrode poles: sleeve, cylinder, sphere, olive-shaped, hemispherical, Spiral, mushroom shape.

Fixing at the heart by: threads, eyelets, hooks, zig-zag, spirals, surgical suture material, soft plastic knobs, e.g. silicone knobs Connecting cable: wire, strand, coil, cannula, isolated or in protective tubes.

Figure 3:
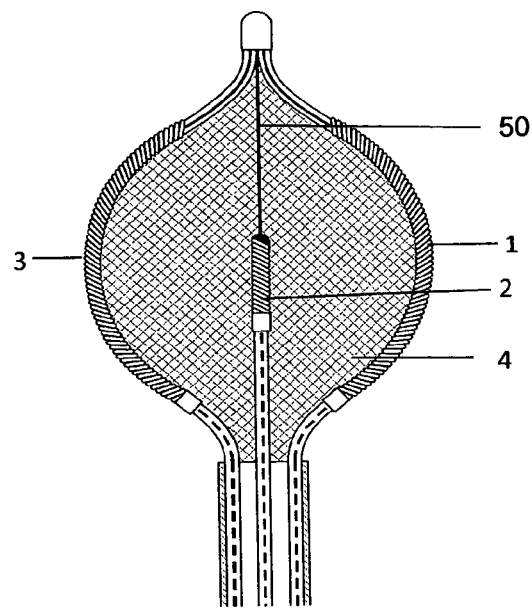
FIG. 3 shows another exemplary electrode assembly for the defibrillation (cardio-version) and stimulation of the heart in the shape of a tennis racket. The electrode poles are metal coils. The entire surface facing away from the heart is isolated.

FIG. 3 shows another exemplary electrode assembly for the defibrillation (cardioversion) and stimulation of the heart in the shape of a tennis racket. The electrodes pole (1) is a metal coil. The entire part of the electrode assembly facing away from the surface of the heart is isolated by a thin polymer membrane (4) so that the field strength distribution is only effective in the direction of the heart. The insulation material is preferably a silicone film.

The different electrode pole (2) is movable along thread (50) in order to find out the best position for the electrode pole (2) and can then be fixed (not shown here).

Figure 4:
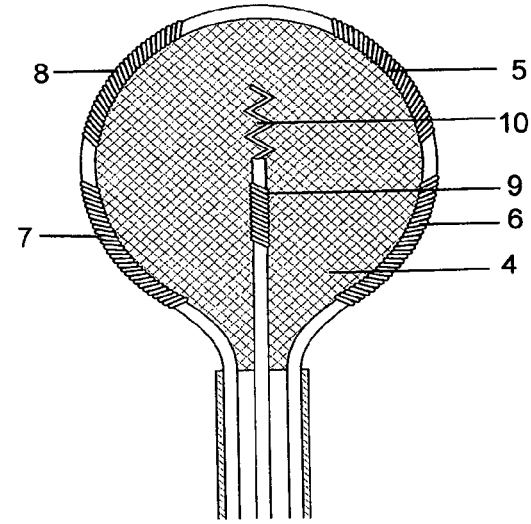
FIG. 4 shows another exemplary electrode assembly for the defibrillation (cardioversion) and stimulation of the heart The electrode poles are metal coil which are circularly arranged. The entire surface of the electrode assembly facing away from the heart is isolated.

FIG. 4 shows another exemplary electrode assembly for the defibrillation (cardioversion) and stimulation of the heart wherein the metal coils (5-9) are arranged circularly in shape of a tennis racket. Through the tennis racket-shaped arrangement of the isolated electrode poles (5-9) it is possible to stimulate various area of the heart, after previous programming thus being able to prevent the occurrence of atrial fibrillation. Again, the side of the electrode assembly facing away from the heart may be isolated by a plastic membrane (4). The electrode assembly which is fixed on the heart must have a stable position when being in use. The stable position is achieved by the helix like shape of electrode pole (10). The helix is designed so that the individual turns are larger in diameter than the diameter of poles (5-9). Because the silicone membrane (4) presses against the helix like shaped electrode pole (10), pole (10) is pressed against the tissue of the heart, and thus a change in position is largely prevented.

On the other hand, the assembly must be easily removable after a few days simply by pulling the assembly through a small opening in the chest.

Figure 5:
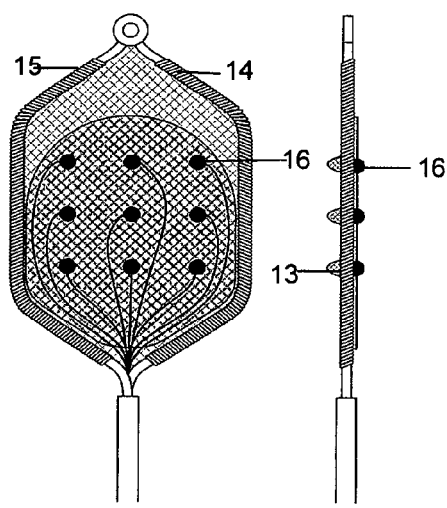
FIG. 5 shows another exemplary electrode assembly for the defibrillation (cardioversion), and multipolar stimulation of the heart. The electrode poles are metal coils which are arranged in shape of a hexagon. The assembly has in addition knobs on the side facing away from the heart. On the side facing to the heart there is an array of electrode poles for mapping and stimulating the areas of the heart.

FIG. 5 shows another exemplary electrode assembly for the defibrillation (cardioversion) and multipolar stimulation at different parts of the heart. The electrode poles are coils (14,15) arranged in shape of a hexagon. The coils have in addition knobs (13) on the side facing away from the heart. The knobs are, for example, made of silicone and avoid an unintended movement of the electrodes. On the side facing to the heart there is an array of electrode poles (16) for mapping and stimulating the areas of the heart.

Figure 6:
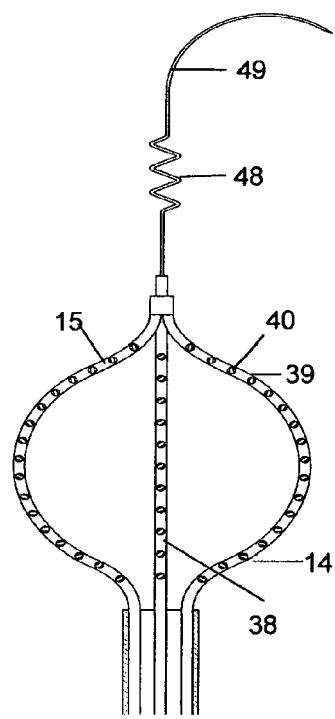
FIG. 6 shows another exemplary electrode assembly for defibrillation (cardioversion), and multipolar stimulation of the heart. The electrode poles are metal coils which are circularly arranged (14,15) and which are integrated in a silicon tube (39). Tube (39) has openings (40) on the side facing the heart.

FIG. 6 shows another exemplary electrode assembly for defibrillation (cardioversion), and multipolar stimulation at different parts of the heart. The electrode poles are coils (14, 15) arranged circularly and being integrated in a silicon tube (39). Tube (39) has openings (40). on the side facing the heart.

The shape and size of the opening and the spacing between the openings is such that the electrode poles are fully effective as defibrillation or stimulation electrode respectively. The inner part of the electrode assembly is also wrapped by a perforated silicone tube (38) so that the individual electrode poles are fully effective on the side facing the heart.

The curved heart needle (49) and the zig-zag-shaped filament (48) serve to fix the epicardial electrode assembly on the heart.

The electrical leads to the electrodes can be arranged both in parallel, coaxial, or one above the other.

Figure 7:
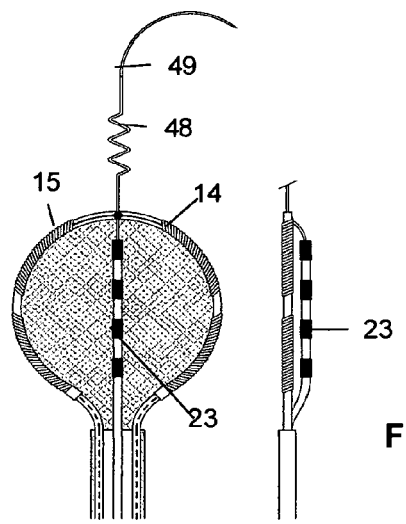
FIG. 7 shows another exemplary electrode assembly for the defibrillation (cardioversion) and multipolar stimulation of the heart. The external electrode poles are metal coils which are circularly arranged. Furthermore there are four electrode poles positioned at the inner region of the assembly and recessed in order to achieve a better fixation on the surface of the heart.

FIG. 7 shows another exemplary electrode assembly for the defibrillation (cardioversion) and multipolar stimulation at different parts of the heart. The electrode poles are metal coils (14, 15) circularly arranged along the outside of the assembly. Furthermore there are four electrode poles (23) which are positioned at the inner region of the assembly and which are recessed in order to achieve a better fixation on the surface of the heart. The curved heart needle (49) and the zig-zag-shaped filament (48) serve to fix the epicardial electrode assembly on the surface of the heart.

Figure 8:
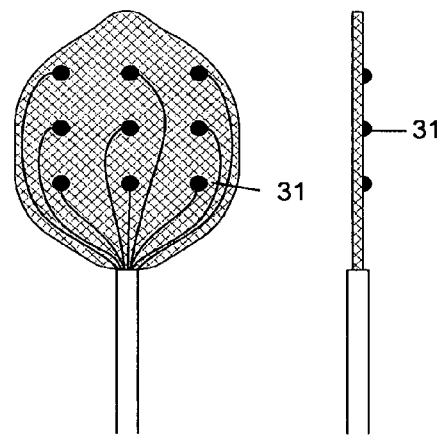
FIG. 8 shows another exemplary electrode assembly for multipolar stimulation of the heart. The electrode assembly is made of silicone rubber and has a number of electrode poles (31).

FIG. 8 shows another exemplary electrode assembly for multipolar stimulation at different parts of the heart which is made of silicone rubber The electrode assembly has a number of electrode poles (31) Such an electrode assembly can easily be pushed under the heart during a surgery due to the biocompatible silicone which is highly flexible. The stimulation electrode can be used separately, but can also be part of the inventive assembly as shown in FIG. 5.

Figure 9:
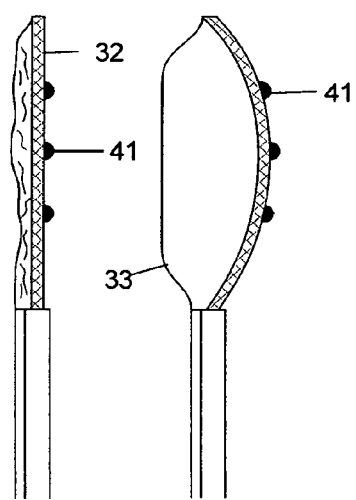
FIG. 9 shows another exemplary electrode assembly (32) which is also made of silicon rubber and which has a plurality of poles (41). A balloon (33) which is positioned behind the electrode area may be expanded when needed to keep the threshold low. The electrode poles are thus pushed against the heart surface when expanding the balloon.

FIG. 9 shows another exemplary electrode assembly (32), also being made of silicon rubber and having a plurality of electrode poles (41).
A balloon (33) which is positioned behind the electrode area may be expanded when needed to keep the threshold low. The electrode poles are thus pushed against the heart surface when expanding the balloon.

Figure 10:
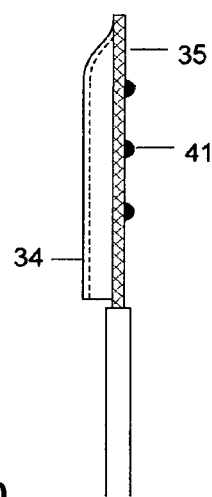
FIG. 10 shows another exemplary electrode assembly (35), which is also made of silicone rubber and which has a plurality of electrode poles (41).

FIG. 10 shows another exemplary electrode assembly (35), which is also made of silicone rubber and which has a plurality of electrode poles (41).
The electrode assembly has a pocket-shaped bulge (34) to achieve a better placement at the surface of the heart. The electrode assembly is moved by a suitable pusher which is in the bulge and which is made of plastic or of metal.

FIG. 11 shows another exemplary electrode assembly (17) for defibrillation (cardioversion) and multipolar stimulation at different parts of the heart. The assembly having the electrodes (18, 19) is cross shaped.

FIG. 12 shows another exemplary electrode assembly (20) for the defibrillation (cardioversion) and multipolar stimulation at different parts of the heart. The assembly having the electrodes (18, 19) is star shaped.

FIG. 13 shows another exemplary electrode assembly (21) for the defibrillation (cardioversion), and multipolar stimulation at different parts of the heart. The assembly is elliptical-like shaped.

The electrode assembly shown in FIG. 11-13 can be used separately for stimulation. However, the assembly can also be part of the inventive electrode assembly. It is possible to attach such a stimulation electrode assembly between circular mounted paddles for defibrillation. Electrode pole 18 may also be formed as a leaf-shaped oak spiral.

FIG. 14 shows another exemplary electrode assembly (22) for the defibrillation (cardioversion) and multipolar stimulation at different parts of the heart. The electrode poles for stimulation are arranged in shape of a fan.

The shaping of the electrode assembly is not limited to the shapes shown above. The shaping can be easily adjusted to the anatomical characteristics.

FIG. 15 shows an example for a connection device connecting the inner electrode assembly and the medical equipment (24) to which the electrode assembly must be connected. The connection device is positioned on the outside of the human body. The connecting leads (25) coming from the inventive electrode assembly are fed to a plastic disk (26)

which is positioned outside the patient's body and fixed on the patient's skin. The disc is elastic due to holes in the disc (shown are 8 holes).

Magnets (28) are integrated at four points of the disc (26) and at the removable cap (24). The magnets ensure that cap (24) is electrically and mechanically fixed to the plastic disc (26).

The connection to the external devices (stimulator, defibrillator) is via a cable connection (100).

FIG. 16 shows an example for a telemetry device (29) the device being positioned outside of the patient's body. The telemetry device is for example a coil which is integrated in cap (24) The telemetry device can store or transfer the data received from the heart or can transfer externally transmitted data, such as electrical pulses or other medical data to the electrode assembly. This telemetry device may also be implanted subcutaneously. Telemetry devices for transmitting medical data are state of the art.

While the apparatus and methods of the subject disclosure have been shown and described with reference to embodiments, those skilled in the art will readily appreciate that changes and/or modifications may be made thereto without departing from the spirit and scope of the subject disclosure.

The invention claimed is:

1. An implantable epicardial electrode assembly configured for use after open heart surgery for the stimulation and cardioversion of left and right atriums of the heart, comprising:
    a plurality of cardioversion electrode poles configured to be fixed on an epicardium layer of the heart, wherein the surface of the cardioversion electrode pole is distributed over an area by arranging the cardioversion electrode poles along a periphery of the electrode assembly wherein the electrode assembly is racket-shaped, circular, elliptical, hexagonal, rectangular, oak leaf-shaped, star-shaped or cloverleaf-shaped, wherein cardioversion takes place between mutually insulated cardioversion electrode poles;
    at least one sensing and/or pacing electrode pole configured to be fixed on the epicardium layer on the heart, wherein the sensing and/or pacing electrode poles are arranged between the cardioversion electrode poles, wherein stimulation of heart tissue can take place between one of the cardioversion electrode poles and the sensing and/or pacing electrode poles; and
    a fixing element configured to fix the electrode assembly to the epicardium layer, said fixing element including a zig-zag shape, tine, loop, V-shaped, or T-bar, wherein the electrode assembly is configured to be removed at any time after use by pulling on an electrical lead of at least one of the cardioversion electrodes and at least one of the sensing and/or pacing electrodes, and wherein the electrode assembly is configured to permit sensing, pacing, and cardioversion in conjunction with a pacemaker or defibrillator being positioned outside a patient body.

2. The implantable epicardial electrode assembly according to claim 1, wherein the electrode poles comprise a metal mesh, metal strand or a metal filament.

3. The implantable epicardial electrode assembly according to claim 1, wherein the sensing and/or pacing electrode pole that is arranged between the cardioversion electrode poles is multi-polar, and wherein the stimulation of the heart can take place between each pole of the multi-polar sensing and/or pacing electrode pole.

4. The implantable epicardial electrode assembly according to claim 1, wherein a part of the electrode assembly facing away from the heart is covered by a stretchable insulating film which comprises silicone.

5. The implantable epicardial electrode assembly according to claim 1, wherein the plurality of electrode poles are integrated into an insulating highly flexible tube said tube having at least one opening for each pole, wherein the opening faces the use position towards the heart.

6. The implantable epicardial electrode assembly according to claim 5, wherein a distance of the electrode poles can vary and wherein liquids or liquid medicine can flow through an opening.

7. The implantable epicardial electrode assembly according to claim 1, wherein the fixing element comprises fixation elements of differing anchor shapes including threads, helix, or loops.

8. The implantable epicardial electrode assembly according to claim 1, wherein all information signals and supplied power for pacing or cardioversion of the heart is stored, and can be wirelessly transmitted in both directions.

* * * * *